United States Patent
Tanaka et al.

(10) Patent No.: US 8,657,888 B2
(45) Date of Patent: Feb. 25, 2014

(54) OXIDATION HAIR DYE COMPOSITION

(75) Inventors: Tomoya Tanaka, Yokohama (JP);
Masashi Watanabe, Yokohama (JP);
Takako Ishii, Yokohama (JP); Kazumi Okubo, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 0 days.

(21) Appl. No.: 13/805,837

(22) PCT Filed: Jun. 23, 2011

(86) PCT No.: PCT/JP2011/064459
§ 371 (c)(1),
(2), (4) Date: Dec. 20, 2012

(87) PCT Pub. No.: WO2011/162358
PCT Pub. Date: Dec. 29, 2011

(65) Prior Publication Data
US 2013/0086756 A1    Apr. 11, 2013

(30) Foreign Application Priority Data
Jun. 23, 2010 (JP) .................. 2010-142524

(51) Int. Cl.
*A61Q 5/10* (2006.01)

(52) U.S. Cl.
USPC ............... 8/405; 8/406; 8/408; 8/435; 8/552; 8/562; 8/580

(58) Field of Classification Search
USPC ............. 8/405, 406, 408, 435, 552, 562, 580
See application file for complete search history.

(56) References Cited

U.S. PATENT DOCUMENTS

2009/0089940 A1*  4/2009  Nonogaki .................. 8/406

FOREIGN PATENT DOCUMENTS

| JP | 64-56611 | 3/1989 |
| JP | 3-20209 | 1/1991 |
| JP | 2000-95647 | 4/2000 |
| JP | 2000-169345 | 6/2000 |
| JP | 2007-153874 | 6/2007 |
| JP | 2008-201727 | 9/2008 |
| JP | 2009-161492 | 7/2009 |

OTHER PUBLICATIONS

STIC Search Report dated Apr. 19, 2013.*
English Translation of the Japanese Patent No. JP 2000-095647 A dated Jul. 22, 2013.*
English Transation of the Japanese Patent No. JP 2008-201727 A dated Jul. 22, 2013.*
English patent abstract for JP Publication No. 64-056611 published Mar. 3, 1989, one page.

(Continued)

*Primary Examiner* — Eisa Elhilo
(74) *Attorney, Agent, or Firm* — Rankin, Hill, & Clark LLP

(57) ABSTRACT

The present invention provides an oxidation hair dye composition that has an excellent hair dyeing effect and less burden on hair. The oxidation hair dye composition of the present invention is characterized by consisting of a first formulation containing an oxidation dye and a second formulation containing an oxidation agent, which is the composition of two formulations that are mixed before use, wherein the first formulation and/or the second formulation contains acetylated hyaluronic acid or salts thereof.

16 Claims, 1 Drawing Sheet

(56) References Cited

OTHER PUBLICATIONS

English patent abstract for JP Publication No. 2007-153874 published Jun. 21, 2007, 13 pages.
Notification Of Transmittal Of International Preliminary Report On Patentability for corresponding PCT/JP2011/064459 mailed Jan. 24, 2013, nine pages.
English abstract for JP 03-020209 published Jan. 29, 1991, one page.
International Search Report for corresponding PCT/JP2011/064459 mailed Sep. 27, 2011, three pages.
Espacenet bibliographic data for JP 2000-095647 published Apr. 4, 2000, one page.
Espacenet bibliographic data for JP 2000169345 published Jun. 20, 2000, one page.
Espacenet bibliographic data for JP 2008-201727 published Sep. 4, 2008, one page.
Espacenet bibliographic data for JP 2009-161492 published Jul. 23, 2009, one page.

* cited by examiner

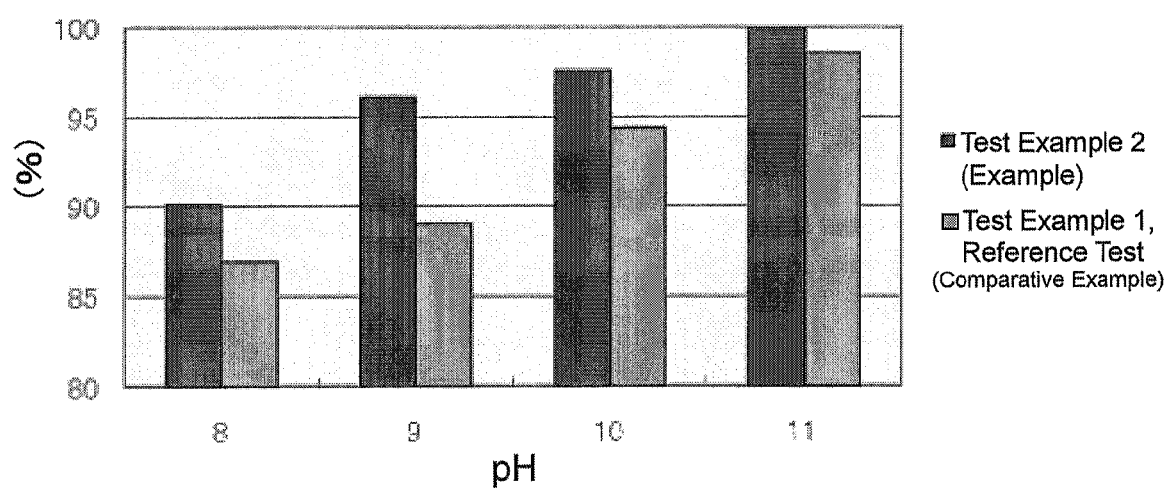

OXIDATION HAIR DYE COMPOSITION

RELATED APPLICATIONS

This application claims the priority of Japanese Patent Application No. 2010-142524 filed on Jun. 23, 2010, which is incorporated herein by reference.

FIELD OF THE INVENTION

The present invention relates to an oxidation hair dye composition, and in particular, relates to an oxidation hair dye composition having an excellent hair dyeing effect and less burden on hair.

BACKGROUND OF THE INVENTION

Among permanent hair dye agent, an oxidation hair dye agent is most commonly used at present. Oxidation dyes contained in the dye agent penetrate hair, undergo oxidation polymerization to exhibit color, and chemically dye the hair, and as a result, the hair dyeing effect is maintained for a long period of time. As a formulation type of an oxidation hair dye agent, a two formulation type in which a first formulation containing an oxidation dye and a second formulation containing an oxidation agent are mixed at the time of use, is generally used.

For improvement of the dyeing property of the oxidation hair dye agent, a blend of mucopolysaccharides like cockscomb-derived hyaluronic acid (Patent Document 1) or microbially-derived hyaluronic acid and salts thereof (Patent Document 2) is known.

Patent literature 1: Japanese unexamined patent publication No. S64-56611 Patent literature 2: Japanese unexamined patent publication No. 2007-153874

DISCLOSURE OF THE INVENTION

Problem to be Solved by the Invention

However, even when the hyaluronic acid is added, it is necessary to have it provided with relatively high pH to obtain a sufficient hair dyeing effect. As such, from the view point of reducing hair damages, it is not necessarily satisfactory.

The present invention was made in view of the above-described conventional art. An object of the invention is to provide an oxidation hair dye composition that has an excellent hair dyeing effect and less burden on hair.

Means to Solve the Problem

The present inventors have diligently studied; as a result, the present inventors have found that an oxidation hair dye composition having an excellent hair dyeing effect and less burden on hair can be obtained by blending acetylated hyaluronic acid.

That is, the oxidation hair dye composition of the present invention is characterized by consisting of a first formulation containing an oxidation dye and a second formulation containing an oxidation agent, which is an oxidation hair dye composition of two formulations that are mixed before use, in which the first formulation and/or the second formulation contains acetylated hyaluronic acid or salts thereof.

In the oxidation hair dye composition, it is preferable that the acetylated hyaluronic acid or salts thereof has a repeating structural unit represented by the following formula (I).

[Formula 1]

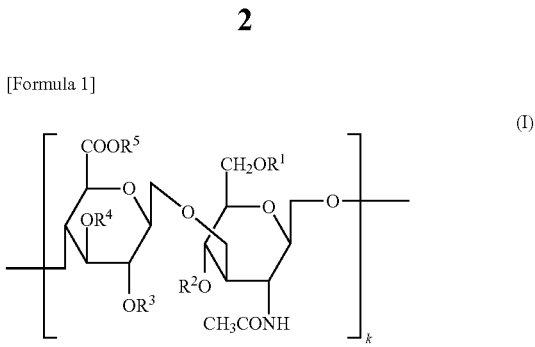

(in the formula, $R^1$, $R^2$, $R^3$, and $R^4$ each independently represent a hydrogen atom or an acetyl group having an ester bond (however, in each repeating structural unit, at least two of $R^1$, $R^2$, $R^3$, and $R^4$ represent an acetyl group on average). $R^5$ represents a hydrogen atom or an alkali metal. k represents the number of 2 or more).

In the oxidation hair dye composition, it is preferable that the blending quantity of the acetylated hyaluronic acid or salts thereof is 0.00001 to 10% by weight.

In the oxidation hair dye composition, it is preferable that the pH of the first formulation is 8 to 11 and the pH of a mixture obtained by mixing in the same weight the first formulation and the second formulation is 8 to 10.

In the oxidation hair dye composition, it is preferable that one or more higher alcohols represented by the following formula (II) are contained.

[Formula 2]

(in the formula, $R^6$ represents an alkyl group expressed as $C_nH_{2n+1}$ and n represents an integer of 0 to 20. $R^7$ represents an alkyl group expressed as $C_mH_{2m+1}$ and m represents an integer of 0 to 20. $R^8$ represents an alkyl group expressed as $C_kH_{2k+1}$ and k represents an integer of 0 to 20. $R^9$ represents an alkylene group expressed as $C_jH_{2j}$ and j represents an integer of 0 to 19. Herein, n+m+k+j=16 to 22, and any two or more of n, m, and k are not simultaneously 0).

In the oxidation hair dye composition, it is preferable that a fatty acid ester that is liquid at room temperature is contained.

Effect of the Invention

The oxidation hair dye composition of the present invention consists of a first formulation containing an oxidation dye and a second formulation containing an oxidation agent, in which the composition contains acetylated hyaluronic acid or salts thereof. Accordingly, the oxidation hair dye composition having a very excellent hair dyeing effect can be provided. Further, compared to conventional cases, as pH can be lowered by 1 or so within a range in which the hair dyeing effect is not affected, hair damages caused by a treatment with a hair dye agent can be reduced, and therefore the oxidation hair dye composition having less burden on hair can be provided.

BRIEF DESCRIPTION OF THE DRAWINGS

FIG. 1 shows the measurement results of colorimeter of the samples shown in the Tables 1 and 2 (Results relative to the test example 2-1).

BEST MODE FOR CARRYING OUT THE INVENTION

The oxidation hair dye composition of the present invention consists of a first formulation containing an oxidation dye and a second formulation containing an oxidation agent, which is an oxidation hair dye composition of two formulations that are mixed before use, in which the first formulation and/or the second formulation contains acetylated hyaluronic acid or salts thereof.

In the following, the present invention is described in detail.

The acetylated hyaluronic acid or salts thereof as an essential component of the oxidation hair dye composition of the present invention is a polymer compound in which hydroxyl groups of hyaluronic acid are partially acetylated. The acetylated hyaluronic acid is a water soluble polymer having a moisturizing effect, and it is known that applying it for a long period of time can exhibit a preventive effect against hair dandruff and itchiness.

By blending the acetylated hyaluronic acid or salts thereof, the oxidation hair dye composition of the present invention exhibits a very excellent hair dyeing effect. Further, as hair damages can be reduced, moisture retention ratio in the hair after dyeing is also high. The acetylated hyaluronic acid may be added to any one of the first formulation and second formulation. However, it is preferably added to the first formulation.

In the present invention, the acetylation degree of the hydroxyl groups of acetylated hyaluronic acid or salts thereof is not specifically limited. However, those having a repeating structural unit represented by the following formula (I) may be preferably used.

[Formula 3]

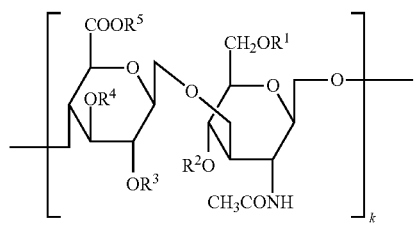

(in the formula, $R^1$, $R^2$, $R^3$, and $R^4$ each independently represent a hydrogen atom or an acetyl group having an ester bond (however, in each repeating structural unit, at least two of $R^1$, $R^2$, $R^3$, and $R^4$ represent an acetyl group on average). $R^5$ represents a hydrogen atom or an alkali metal. k represents the number of 2 or more).

When the acetylation degree is set to 1 for a case in which one of $R^1$ to $R^4$ in the formula (I) is an acetyl group, acetylated hyaluronic acid having acetylation degree of from 2 to 4 is preferably used in the present invention.

Further, molecular weight of the acetylated hyaluronic acid used in the present invention is preferably 10,000 to 1,000,000 in hyaluronic acid equivalent.

The acetylated hyaluronic acid or salts thereof used in the present invention can be produced by a method like, for example, a method in which hyaluronic acid in powder state is dispersed in acetic acid and trifluoroacetic anhydride is added as a catalyst for the reaction, a method in which hyaluronic acid is dispersed in acetic acid, p-toluene sulfonic acid is added thereto, and acetic anhydride is further added for the reaction, and a method in which hyaluronic acid is suspended in acetic anhydride solvent and added with conc. sulfuric acid for the reaction (Japanese Patent Application Laid-Open Nos. 6-9707 and 8-53501, etc.). However, it is not limited to the methods exemplified.

In the oxidation hair dye composition of the present invention, the upper limit of the blending quantity of acetylated hyaluronic acid or salts is preferably 10% by weight and more preferably 1% by weight considering the viscosity of the hair dye agent and etc. Meanwhile, the lower limit of the blending quantity is preferably 0.00001% by weight and more preferably 0.0001% by weight considering the hair dyeing effect.

The oxidation hair dye composition of the present invention containing the acetylated hyaluronic acid or salts thereof has an excellent hair dyeing effect, which can be exhibited even in a low pH range. By lowering pH that is generally regarded as one factor causing hair damages by a hair dye agent, it becomes possible to inhibit the hair damages.

That is, in the oxidation hair dye composition of the present invention, it is preferable that pH of the first formulation is adjusted to 8 to 11 and pH of a mixture obtained by mixing in the same weight the first formulation and the second formulation is adjusted to 8 to 10. Also, pH of a mixture obtained by mixing in the same weight the first formulation and the second formulation is more preferably adjusted to about 8 to 9 and most preferably adjusted to about 9 considering the inhibition of further hair damages.

Examples of the pH adjusters include alkali metal salts (for example, sodium salts and potassium salts) of inorganic acids such as phosphoric acid, sulfuric acid, hydrochloric acid, and carbonic acid or organic acids such as citric acid, glycolic acid, and tartaric acid; and organic alcali salts such as ammonia, monoethanolamine, diethanolamine, triethanolamine, and aminomethyl propanol. The pH can be adjusted by using one or more pH adjusters.

In the oxidation hair dye composition of the present invention, it is necessary to contain an oxidation dye in the first formulation.

Examples of the oxidation dyes include p-diamines such as p-phenylenediamine, p-toluylenediamine, N-methyl-p-phenylenediamine, N, N-dimethyl-p-phenylenediamine, N,N-diethyl-2-methyl-p-phenylenediamine, N-ethyl-N-hydroxyethyl-p-phenylenediamine, chloro-p-phenylenediamine, N, N-bis-(2-hydroxyethyl)-p-phenylenediamine, methoxy-p-phenylenediamine, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine, and N-(2-methoxyethyl)-p-phenylenediamine; 2,5-diaminopyridines; p-aminophenols such as p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2,4-diaminophenol, and 5-aminosalicylic acid; o-aminophenols; o-phenylenediamines; α-naphtol, o-cresol, m-cresol, 2,6-dimethylphenol, 2,5-dimethylphenol, 3,4-dimethylphenol, 3,5-dimethylphenol, benzcatechin, pyrogallol, 1,5-dihydroxynaphthalene, 1,7-dihydroxynaphthalene, 5-amino-2-methylphenol, hydroquinone, 2,4-diaminoanisole, m-toluylenediamine, 4-aminophenol, resorcinol, resorcinol monomethyl ether, m-phenylenediamine, 1-phenyl-3-methyl-5-pyrazolone, 1-phenyl-3-amino-5-pyrazolone, 1-phenyl-3,5-dimethylpyrazolidine, 1-methyl-7-dimethylamino-4-hydroxy-2-chinolon, m-aminophenol, 4-chlororesorcinol, 2-methylresorcinol, 2,4-diaminophenoxyethanol, 3,5-diamino-trifluoromethylbenzene, 2,4-diamino-fluorobenzene, 3,5-diamino-fluorobenzene, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine, 2,6-diaminopyrimidine and salts thereof. The blending quantity of the oxidation dye is not specifically limited if it is within the range in which it is normally used in oxidation hair dye agents.

In the oxidation hair dye composition of the present invention, it is necessary to contain a peroxidative agent in the second formulation.

Examples of the peroxidative agents used in the present invention include hydrogen peroxide, persulfate, percarbonate, perborate, bromate, periodate, and urea peroxide. The blending quantity of the peroxidative agent is not specifically limited if it is within the range in which it is normally used in oxidation hair dye agents.

Further, according to the oxidation hair dye agent of the present invention, it is preferable that oils are contained in at least one of the first formulation and the second formulation.

As oils blended in the oxidation hair dye composition of the present invention, one or more oils represented by the following formula (II) are preferably used.

[Formula 4]

(II)

(in the formula, $R^6$ represents an alkyl group expressed as $C_nH_{2n+1}$ and n represents an integer of 0 to 20. $R^7$ represents an alkyl group expressed as $C_mH_{2m+1}$ and m represents an integer of 0 to 20. $R^8$ represents an alkyl group expressed as $C_kH_{2k+1}$ and k represents an integer of 0 to 20. $R^9$ represents an alkylene group expressed as $C_jH_{2j}$ and j represents an integer of 0 to 19. Herein, $n+m+k+j=16$ to 22, and any two or more of n, m, and k are not simultaneously 0).

Among the oils that are represented by the formula (II), it is preferable to blend a branched alcohol having 16 to 22 carbon atoms. It is more preferable to blend 2-decyl tetradecanol, lanolin alcohol, hexyl decanol, octyl dodecanol, and isostearyl alcohol. It is most preferable to blend isostearyl alcohol.

In the oxidation hair dye composition of the present invention, the blending quantity of oil represented by the formula (II) is not specifically limited and can be used with appropriate adjustment if it is within the range in which the effect of the present invention is obtained. However, it is preferably 0.01 to 10% by weight and especially preferably 0.1 to 5% by weight.

In the oxidation hair dye composition of the present invention, it is preferable to blend one or more fatty acid esters that are liquid at room temperature. Examples of the fatty acid esters that are liquid at room temperature include isostearyl erucate, octyldodecyl erucate, oleyl erucate, stearyl erucate, behenyl erucate, isostearyl isostearate, isocetyl isostearate, decyl isostearate, butyl isostearate, hexyl isostearate, myristyl isostearate, lauryl isostearate, isocetyl isodecanoate, isodecyl isononanoate, isotridecyl isononanoate, isononyl isononanoate, octyl isopalmitate, octyl isopelargonate, isodecyl oleate, isopropyl oleate, ethyl oleate, octyldodecyl oleate, oleyl oleate, decyl oleate, butyl oleate, and methyl oleate.

Among the fatty acid esters that are liquid at room temperature, it is preferable to blend unsaturated fatty acid ester. It is more preferable to blend oleyl erucate, oleyl oleate, decyl oleate, and isodecyl oleate and most preferable to blend decyl oleate.

In the oxidation hair dye composition of the present invention, the blending quantity of fatty acid ester that is liquid at room temperature is not specifically limited and can be used with appropriate adjustment if it is within the range in which the effect of the present invention is obtained. However, it is preferably 0.01 to 10% by weight and especially preferably 0.1 to 5% by weight.

In the oxidation hair dye composition of the present invention, the blending quantity of oil is not specifically limited and can be used with appropriate adjustment if it is within the range in which the effect of the present invention is obtained. However, it is preferably 0.1 to 80% by weight and especially preferably 1 to 50% by weight.

In the oxidation hair dye composition of the present invention, other components normally used in hair dye compositions can be blended if they are within the range in which the effect of the present invention is not undermined.

For example, as the components blended in the first formulation, examples of moisturizers include glycerine, propylene glycol, dipropylene glycol, polyethylene glycol, chondroitin sulfate, hyaluronate, diglycerine, 1,3-butylene glycol, pyrolidone carboxylate, sorbitol, maltitol, lactose, and oligosaccharide, and examples of oils include shea butter, squalane, lecithin, liquid paraffin, vaseline, higher fatty acid, triglyceride, and ester oil.

Also, examples of lower alcohols include ethanol, butanol, propanol, isopropanol, and benzyl alcohol, and examples of higher alcohols include 2-ethylhexyl alcohol, cetostearyl alcohol, lauryl alcohol, behenyl alcohol, stearyl alcohol, and cetyl alcohol.

Also, antioxidants and stabilizers such as thioglycolate, L-ascorbate, bisulfite, hydrosulfite salt, and hydrogen sulfate; protein hydrolysates and quaternized compounds thereof such as collagen hydrolysate, keratin hydrolysate, silk protein hydrolysate, elastin hydrolysate, and soya bean protein hydrolysate; and alkali agents such as ammonia water, alkanolamine, ammonium carbonate, sodium hydrogen carbonate, and potassium hydroxide can be blended.

Also, as an emulsifier, amphiphilic agent or surfactant may be used.

Examples of nonionic surfactants include polyoxyethylene surfactants such as polyoxyethylene alkyl ether, polyoxyethylene fatty acid ester, polyoxyethylene polyhydric alcohol fatty acid partial ester, and polyoxyethylene hydrogenated castor oil derivative; alkylpolyglycosides such as octylpolyglycoside; polyglycerine surfactants such as polyglycerine fatty acid ester and polyglycerine alkyl ether; sugar alcohol hydroxyalkyl ethers such as maltitol hydroxyalkyl ether; and fatty acid diethanolamide.

Also, anion surfactants such as higher fatty acid salts, alkyl benzene sulfonates, phosphoesters, alkyl sulfates, alkyl sulfate esters, and polyoxyethylene alkyl sulfates; cation surfactants such as amino acids, alkyltrimethyl ammonium salt, dialkyldimethylammonium salt, and alkyldimethylamine oxide; and other surfactants can be blended.

Also, examples of sequestering agents and antiseptic agents include hydroxyethane diphosphonates, phenacetin, ethylenediaminetetraacetate and its salts, parabens, and stannates.

Examples of the polymer compound include a poly(dimethylallyl ammonium halide) type cationic polymer, a condensation product type cationic polymer of polyethylene glycol, epichlorohydrin, propylene amine, and talloyl amine obtained from tallow fatty acids, a co-polymer type cationic polymer of polyethylene glycol, vinyl pyrrolidone, and dimethylamino methacrylate, and quaternary nitrogen-containing cellulose ether type cationic polymers.

Also, thickeners such as lauric acid diethanolamide, carboxymethyl cellulose, carboxyvinyl polymer, hydroxyethyl cellulose, hydroxypropyl cellulose, methyl cellulose, xanthan gum, carrageenan, alginate, pectin, furcellaran, gum arabic, gutch gum, karaya gum, gum tragacanth, agar powder, bentonite, and cross-linked polyacrylate can be blended if they are within the range in which the effect of the present invention is not undermined.

And also, perfume, agent, coloring agent, UV protective agent, water, and etc can also be blended. These components are appropriately selected and added as required, and are not specifically limited.

As the components blended in the second formulation, examples of such components include sequestering agents such as ethylenediaminetetraacetate and its salts, and stannates; antiseptic agents such as phenacetin and parabens; oils such as liquid paraffin and vaseline; higher alcohols such as 2-ethylhexyl alcohol, cetostearyl alcohol, lauryl alcohol, stearyl alcohol, and cetyl alcohol; surfactants such as polyoxyethylene alkyl ethers, alkyl sulfate esters, and sodium acyl methyl taurines; acids such as organic acids (for example, citric acid, malic acid, acetic acid, lactic acid, oxalic acid, tartaric acid, formic acid, and levulinic acid) and inorganic acids (for example, phosphone acid and hydrochloric acid); perfume, agent; coloring agent; and water. These components are appropriately selected and added as required, however are not specifically limited.

Further, regarding the mixing ratio between the first formulation and the second formulation in the oxidation hair dye composition, it is general that first formulation:second formulation=1:1 in terms of weight ratio. However, as long as there is no problem in hair dyeing effect, flowness, usability, and even dyeing property, it is not specifically limited.

EXAMPLES

The present invention will be further described in the following examples. However, the invention is not limited by these examples. Unless otherwise specified, the blending quantity of each component will be expressed in % by weight.

Prior to illustrating the examples, the methods for the evaluation tests used in the present invention will be explained.

Each oxidation hair dye composition (first formulation and second formulation) with the blending composition shown in Table 1 was produced by the following production method. Further, pH of the first formulation was adjusted to the given pH by appropriately blending a pH adjusting agent.

Also, regarding the evaluation item (1), the evaluation was made based on the following scoring criteria and pH was measured at the time of mixing the first formulation and the second formulation. The results are shown in Table 1.

Production Method of Oxidation Hair Dye Composition
(First Formulation)

The entire components were dissolved by heating at 80° C. under stirring. After emulsification followed by cooling, the first formulation was obtained.

(Second Formulation)

Components other than hydrogen peroxide were dissolved by heating at 80° C. under stirring. After emulsification, when it is cooled to 40° C., hydrogen peroxide was added and stirred until it becomes homogeneous. As a result, the second formulation was obtained.

Evaluation (1): Dyeing Test

The first formulation and the second formulation were mixed well with each other in an amount of 10 g and 10 g, respectively. White hair truss (1 g) was impregnated in the mixture liquid. After keeping it for 30 min at room temperature, the hair truss was washed well with warm water and dried.

Dyeing of hair truss in the Reference Test was set to (5) as reference value, and dyeing of the hair truss in the Test Examples was evaluated by sensory evaluation based on 5-level naked eye determination.

5 . . . Equivalent to the hair truss of the Reference Test.
4 . . . Slightly lighter than the hair truss of the Reference Test.
3 . . . Little lighter than the hair truss of the Reference Test.
2 . . . Lighter than the hair truss of the Reference Test.
1 . . . Considerably lighter than the hair truss of the Reference Test.

TABLE 1

| | | Test Example | | |
|---|---|---|---|---|
| | Reference Test | 1-1 | 1-2 | 1-3 |
| First formulation | | | | |
| Microbially-derived sodium hyaluronate | 0.0001 | 0.0001 | 0.0001 | 0.0001 |
| Cetostearyl alcohol | 5.0 | 5.0 | 5.0 | 5.0 |
| Propylene glycol | 3.0 | 3.0 | 3.0 | 3.0 |
| POE cetyl ethyl ether | 5.0 | 5.0 | 5.0 | 5.0 |
| Anhydrous sodium sulfite | 0.2 | 0.2 | 0.2 | 0.2 |
| p-phenylenediamine | 0.5 | 0.5 | 0.5 | 0.5 |
| Resorcinol | 0.5 | 0.5 | 0.5 | 0.5 |
| Purified water | balance | balance | balance | balance |
| Ammonia (28%) | 5.0 | 4.0 | 3.0 | 1.0 |
| pH adjuster | proper quantity | proper quantity | proper quantity | proper quantity |
| pH (first formulation) | 11 | 10 | 9 | 8 |
| Second formulation | | | | |
| 35% hydrogen peroxide water | 16.5 | 16.5 | 16.5 | 16.5 |
| Cetostearyl alcohol | 3.0 | 3.0 | 3.0 | 3.0 |
| POE cetyl ethyl ether | 2.0 | 2.0 | 2.0 | 2.0 |
| Tetrasodium edetate | 0.02 | 0.02 | 0.02 | 0.02 |
| Purified water | balance | balance | balance | balance |
| Evaluation (1): Dyeing test | Reference (5) | 4 | 3 | 2 |
| pH at the time of mixing | 10 | 9 | 9 | 8 |

As a result of performing, as a Reference Test, the test with a conventional oxidation hair dye agent in which microbially-derived sodium hyaluronate is blended, the sample of the Reference Test represents an excellent hair dyeing effect.

However, according to the Test Examples 1-1 to 1-3 having the same composition as the Reference Test, with decrease in pH of the composition by lowering the pH of the first formulation, the hair dyeing effect was reduced.

Thus, when an oxidation hair dye composition is expected to have a hair dyeing effect, it is generally to have high pH, i.e., strongly alkaline. However, there is a concern that bad influence on hair is yielded according to application of a strongly alkaline composition to hair.

Further, it was made clear in the past that addition of microbially-derived hyaluronic acid, which is known as a component for enhancing a hair dyeing effect, is effective in high pH region only and the hair dyeing effect is poor in low pH region.

The present inventors studied blending component which can achieve excellent hair dyeing effect in low pH region.

Each oxidation hair dye composition (first formulation and second formulation) with the blending composition shown in Table 2 was produced by the above-described production method. Further, pH of the first formulation was adjusted to the given pH by appropriately blending a pH adjusting agent.

Also, regarding the evaluation item (1), the evaluation was made based on the above-described scoring criteria and pH was measured at the time of mixing the first formulation and the second formulation. The results are shown in Table 2.

Next, the oxidation hair dye compositions of the Reference Test and each Test Example shown in Tables 1 and 2 were measured by using a colorimeter CM-3600 (manufactured by Konica Minolta Holdings, Inc.). When the measurement value of the Test Example 2-1 (i.e., Test Example 2 (example) •pH 11 in the FIGURE) is 100%, the value (%) calculated from each measurement value is represented in FIG. 1.

According to FIG. 1, also from the measurement value obtained by using a colorimeter, an excellent hair dyeing effect was observed for the sample of the Test Example 2, similar to the results obtained from the naked eye evaluation. Further, in any pH region, the oxidation hair dye composition of the present invention in which acetylated sodium hyaluronate was blended exhibited better hair dyeing effect than the Reference Test and the sample of the Test Example 1.

Further, it was made clear that, even when pH is lowered by 1 or so, the oxidation hair dye composition of the present invention is expected to represent a hair dyeing effect that is

TABLE 2

|  | Reference Test | Test Example | | | |
|---|---|---|---|---|---|
|  |  | 2-1 | 2-2 | 2-3 | 2-4 |
| First formulation | | | | | |
| Microbially-derived sodium hyaluronate | 0.0001 | — | — | — | — |
| Acetylated sodium hyaluronate | — | 0.0001 | 0.0001 | 0.0001 | 0.0001 |
| Cetostearyl alcohol | 5.0 | 5.0 | 5.0 | 5.0 | 5.0 |
| Propylene glycol | 3.0 | 3.0 | 3.0 | 3.0 | 3.0 |
| POE cetyl ethyl ether | 5.0 | 5.0 | 5.0 | 5.0 | 5.0 |
| Anhydrous sodium sulfite | 0.2 | 0.2 | 0.2 | 0.2 | 0.2 |
| p-phenylenediamine | 0.5 | 0.5 | 0.5 | 0.5 | 0.5 |
| Resorcinol | 0.5 | 0.5 | 0.5 | 0.5 | 0.5 |
| Purified water | balance | balance | balance | balance | balance |
| Ammonia (28%) | 5.0 | 5.0 | 4.0 | 3.0 | 1.0 |
| pH adjuster | proper quantity | proper quantity | proper quantity | proper quantity | proper quantity |
| pH (first formulation) | 11 | 11 | 10 | 9 | 8 |
| Second formulation | | | | | |
| 35% hydrogen peroxide water | 16.5 | 16.5 | 16.5 | 16.5 | 16.5 |
| Cetostearyl alcohol | 3.0 | 3.0 | 3.0 | 3.0 | 3.0 |
| POE cetyl ethyl ether | 2.0 | 2.0 | 2.0 | 2.0 | 2.0 |
| Tetrasodium edetate | 0.02 | 0.02 | 0.02 | 0.02 | 0.02 |
| Purified water | balance | balance | balance | balance | balance |
| Evaluation (1): Dyeing test | Reference (5) | 5 | 5 | 5 | 4 |
| pH at the time of mixing | 10 | 10 | 9 | 9 | 8 |

According to the Test Examples 2-1 to 2-4 in which acetylated sodium hyaluronate is blended, the hair dyeing effect is not much reduced even when pH is lowered. When pH of the first formulation is 9 to 11 and pH of the composition is 9 to 10, an oxidation hair dye agent having a hair dyeing effect equivalent to the Reference Test was obtained.

Accordingly, in the oxidation hair dye composition of the present invention, it is necessary to contain an acetylated sodium hyaluronate.

Further, it was made clear that, in a high pH region, the oxidation hair dye composition of the present invention in which acetylated sodium hyaluronate is blended has almost the same hair dyeing effect as a conventional composition to which microbially-derived hyaluronic acid is blended, but in a low pH region, a significant difference is represented.

Therefore, in light of reducing hair damages, in the oxidation hair dye composition of the present invention, it is preferable that pH of the first formulation is adjusted to 8 to 11 and pH of a mixture obtained by mixing in the same weight the first formulation and the second formulation is adjusted to 8 to 10.

equivalent to or greater than a conventional oxidation hair dye composition having one level higher pH value.

Next, a difference in hair dyeing effect between the conventional hyaluronic acid and the acetylated hyaluronic acid of the present invention in a pH region lower than the conventional oxidation hair dye agent (i.e., pH 10 for the first formulation and pH 9 for the composition) was confirmed and also discussion regarding an blending quantity and other components was made.

Each oxidation hair dye composition (first formulation and second formulation) with the blending composition shown in Table 3 was produced by the above-described production method. Then, it was evaluated for the evaluation items (2) and (3) in the following evaluation criteria. The results are shown in Table 3.

Evaluation (2): Dyeing Test

The first formulation and the second formulation were mixed well with each other in an amount of 10 g and 10 g, respectively. White hair truss (1 g) was impregnated in the mixture liquid. After keeping it for 30 min at room temperature, the hair truss was washed well with warm water and dried.

Dyeing of control hair truss set to (0) as reference value, and dyeing of the hair truss in the Test Examples was evaluated by sensory evaluation based on 5-level naked eye determination.

4 . . . Much better dyeing was obtained compared to the control hair truss.
3 . . . Better dyeing was obtained compared to the control hair truss.
2 . . . Dyeing was obtained compared to the control hair truss.
1 . . . Slightly dyeing was obtained compared to the control hair truss.
0 . . . Equivalent to the control hair truss.

Evaluation (3): Moisture Retention Ratio

The hair truss dyed according to the evaluation item (2) was left to stand for 12 hours at 80% relative humidity and its weight (W1) was measured. In addition, after drying under reduced pressure for 2 hours, weight (W2) of the same hair truss was measured. The following moisture retention ratio was calculated by these measurement values.

$$\text{Moisture retention ratio}(\%)=(W1-W2)\times 100/W1$$

TABLE 3

| | Control | Test Example 3-1 | 3-2 | 3-3 | 3-4 | 3-5 | 3-6 | 3-7 | 3-8 | 3-9 |
|---|---|---|---|---|---|---|---|---|---|---|
| First formulation | | | | | | | | | | |
| Cockscomb-derived sodium hyaluronate | — | 0.0001 | — | — | — | — | — | — | — | — |
| Microbially-derived sodium hyaluronate | — | — | 0.0001 | — | — | — | — | — | — | — |
| Acetylated sodium hyaluronate | — | — | — | 0.0001 | 0.00001 | 0.001 | 0.01 | 0.0001 | 0.0001 | 0.0001 |
| Isostearyl alcohol | — | — | — | — | — | — | — | 1.0 | — | 1.0 |
| Decyl oleate | — | — | — | — | — | — | — | — | 1.0 | 1.0 |
| Cetostearyl alcohol | 5.0 | 5.0 | 5.0 | 5.0 | 5.0 | 5.0 | 5.0 | 5.0 | 5.0 | 5.0 |
| Propylene glycol | 3.0 | 3.0 | 3.0 | 3.0 | 3.0 | 3.0 | 3.0 | 3.0 | 3.0 | 3.0 |
| POE cetyl ethyl ether | 5.0 | 5.0 | 5.0 | 5.0 | 5.0 | 5.0 | 5.0 | 5.0 | 5.0 | 5.0 |
| Anhydrous sodium sulfite | 0.2 | 0.2 | 0.2 | 0.2 | 0.2 | 0.2 | 0.2 | 0.2 | 0.2 | 0.2 |
| p-phenylenediamine | 0.5 | 0.5 | 0.5 | 0.5 | 0.5 | 0.5 | 0.5 | 0.5 | 0.5 | 0.5 |
| Resorcin | 0.5 | 0.5 | 0.5 | 0.5 | 0.5 | 0.5 | 0.5 | 0.5 | 0.5 | 0.5 |
| Purified water | balance | balance | balance | balance | balance | balance | balance | balance | balance | balance |
| Ammonia (28%) | 5.0 | 5.0 | 5.0 | 5.0 | 5.0 | 5.0 | 5.0 | 5.0 | 5.0 | 5.0 |
| pH adjuster | proper quantity | proper quantity | proper quantity | proper quantity | proper quantity | proper quantity | proper quantity | proper quantity | proper quantity | proper quantity |
| pH(first formulation) | 10 | 10 | 10 | 10 | 10 | 10 | 10 | 10 | 10 | 10 |
| Second formulation | | | | | | | | | | |
| 35% hydrogen peroxide water | 16.5 | 16.5 | 16.5 | 16.5 | 16.5 | 16.5 | 16.5 | 16.5 | 16.5 | 16.5 |
| Cetostearyl alcohol | 3.0 | 3.0 | 3.0 | 3.0 | 3.0 | 3.0 | 3.0 | 3.0 | 3.0 | 3.0 |
| POE cetyl ethyl ether | 2.0 | 2.0 | 2.0 | 2.0 | 2.0 | 2.0 | 2.0 | 2.0 | 2.0 | 2.0 |
| Tetrasodium edetate | 0.02 | 0.02 | 0.02 | 0.02 | 0.02 | 0.02 | 0.02 | 0.02 | 0.02 | 0.02 |
| Purified water | balance | balance | balance | balance | balance | balance | balance | balance | balance | balance |
| Evaluation (2): Dyeing test | Reference (0) | 1 | 1 | 3 | 2 | 3 | 4 | 3 | 3 | 4 |
| Evaluation (3): Moisture retention ratio | 44.1 | — | 47.7 | 50.3 | — | — | — | — | — | — |
| pH at the time of mixing | 9 | 9 | 9 | 9 | 9 | 9 | 9 | 9 | 9 | 9 |

According to Table 3, the test examples 3-1 and 3-2 in which cockscomb-derived or microbially-derived sodium hyaluronate is added to an oxidation hair dye agent as a control represented better dyeing than the control. However, there still is a need for improving the hair dyeing effect.

On the other hand, sample of the test example 3-3 in which acetylated sodium hyaluronate is added in the same amount as the test examples 3-1 and 3-2 to an oxidation hair dye agent as a control had an excellent hair dyeing effect like the results given above.

The test example 3-4 containing less blending quantity of acetylated hyaluronic acid also represented better hair dyeing effect than the test examples 3-1 and 3-2.

In addition, according to the test examples 3-5 and 3-6, it was found that the hair dyeing effect can be improved by increasing blending quantity of acetylated hyaluronic acid.

In addition, according to the test examples 3-7 to 3-9, an excellent hair dyeing effect can be obtained from a sample in which isostearyl alcohol and/or decyl oleate is further added to an oxidation hair dye agent to which acetylated sodium hyaluronate is added.

In addition, according to the moisture retention test of the test examples 3-2 and 3-3, it was clear that, when hair is dyed by using the oxidation hair dye composition of the present invention to which acetylated sodium hyaluronate is added, high after-dyeing moisture retention ratio is obtained from the dyed hair.

What is claimed is:

1. An oxidation hair dye composition consisting of a first formulation containing an oxidation dye and a second formulation containing an oxidation agent, which is the composition of two formulations that are mixed before use, wherein the first formulation and/or the second formulation contains acetylated hyaluronic acid or salts thereof and the pH of a mixture of the first formulation and the second formulation in the same weight is 8 to 9.

2. The oxidation hair dye composition according to claim 1, wherein the acetylated hyaluronic acid or salts thereof has a repeating structural unit represented by the following formula (I):

[Formula I]

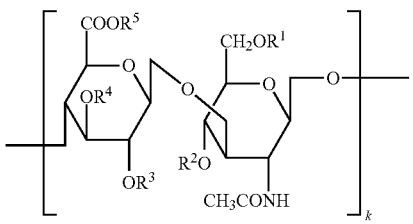

in the formula, $R^1$, $R^2$, $R^3$, and $R^4$ each independently represent a hydrogen atom or an acetyl group having an ester bond, however, in each repeating structural unit, at least two of $R^1$, $R^2$, $R^3$, and $R^4$ represent an acetyl group on average, $R^5$ represents a hydrogen atom or an alkali metal, k represents the number of 2 or more.

3. The oxidation hair dye composition according to claim 2, wherein the blending quantity of the acetylated hyaluronic acid or salts thereof is 0.00001 to 10% by weight.

4. The oxidation hair dye composition according to claim 3, wherein the pH of the first formulation is 8 to 11.

5. The oxidation hair dye composition according to claim 4, wherein one or more higher alcohols represented by the following formula (II) are contained:

[Formula II]

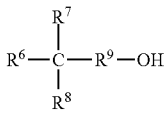

in the formula, $R^6$ represents an alkyl group expressed as $C_nH_{2n+1}$ and n represents an integer of 0 to 20, $R^7$ represents an alkyl group expressed as $C_mH_{2m+1}$ and m represents an integer of 0 to 20, $R^8$ represents an alkyl group expressed as $C_kH_{2k+1}$ and k represents an integer of 0 to 20, $R^9$ represents an alkylene group expressed as $C_jH_{2j}$ and j represents an integer of 0 to 19, wherein n+m+k+j=16 to 22, and any two or more of n, m, and k are not simultaneously 0.

6. The oxidation hair dye composition according to claim 5, wherein a fatty acid ester that is liquid at room temperature is contained.

7. The oxidation hair dye composition according to claim 1, wherein the blending quantity of the acetylated hyaluronic acid or salts thereof is 0.00001 to 10% by weight.

8. The oxidation hair dye composition according to claim 7, wherein the pH of the first formulation is 8 to 11.

9. The oxidation hair dye composition according to claim 8, wherein one or more higher alcohols represented by the following formula (II) are contained:

[Formula II]

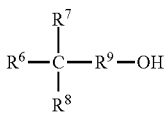

in the formula, $R^6$ represents an alkyl group expressed as $C_nH_{2n+1}$ and n represents an integer of 0 to 20, $R^7$ represents an alkyl group expressed as $C_mH_{2m+1}$ and m represents an integer of 0 to 20, $R^8$ represents an alkyl group expressed as $C_kH_{2k+1}$ and k represents an integer of 0 to 20, $R^9$ represents an alkylene group expressed as $C_jH_{2j}$ and j represents an integer of 0 to 19, wherein n+m+k+j 16 to 22, and any two or more of n, m, and k are not simultaneously 0.

10. The oxidation hair dye composition according to claim 9, wherein a fatty acid ester that is liquid at room temperature is contained.

11. The oxidation hair dye composition according to claim 1, wherein the pH of the first formulation is 8 to 11.

12. The oxidation hair dye composition according to claim 11, wherein one or more higher alcohols represented by the following formula (II) are contained:

[Formula II]

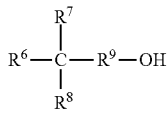

in the formula, $R^6$ represents an alkyl group expressed as $C_nH_{2n+1}$ and n represents an integer of 0 to 20, $R^7$ represents an alkyl group expressed as $C_mH_{2m+1}$ and m represents an integer of 0 to 20, $R^8$ represents an alkyl group expressed as $C_kH_{2k+1}$ and k represents an integer of 0 to 20, $R^9$ represents an alkylene group expressed as $C_jH_{2j}$ and j represents an integer of 0 to 19, wherein n+m+k+j=16 to 22, and any two or more of n, m, and k are not simultaneously 0.

13. The oxidation hair dye composition according to claim 12, wherein a fatty acid ester that is liquid at room temperature is contained.

14. The oxidation hair dye composition according to claim 1, wherein one or more higher alcohols represented by the following formula (II) are contained:

[Formula II]

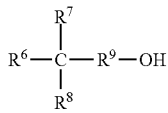

in the formula, $R^6$ represents an alkyl group expressed as $C_nH_{2n+1}$ and n represents an integer of 0 to 20, $R^7$ represents an alkyl group expressed as $C_mH_{2m+1}$ and m represents an integer of 0 to 20, $R^8$ represents an alkyl group expressed as $C_kH_{2k+1}$ and k represents an integer of 0 to 20, $R^9$ represents an alkylene group expressed as $C_jH_{2j}$ and j represents an integer of 0 to 19, wherein n+m+k+j=16 to 22, and any two or more of n, m, and k are not simultaneously 0.

15. The oxidation hair dye composition according to claim 14, wherein a fatty acid ester that is liquid at room temperature is contained.

16. The oxidation hair dye composition according to claim 1, wherein a fatty acid ester that is liquid at room temperature is contained.

* * * * *